United States Patent [19]
Morgan et al.

[11] Patent Number: 5,785,714
[45] Date of Patent: *Jul. 28, 1998

[54] METHOD OF ACL RECONSTRUCTION USING DOUBLE SOCKET GRAFT PLACEMENT AND FIXATION

[75] Inventors: Craig D. Morgan, Greenville, Del.; Reinhold Schmieding, Naples, Fla.

[73] Assignee: Arthrex, Inc., Naples, Fla.

[ * ] Notice: The term of this patent shall not extend beyond the expiration date of Pat. No. 5,603,716.

[21] Appl. No.: 801,635

[22] Filed: Feb. 18, 1997

[51] Int. Cl.$^6$ .................................................. A61B 17/58
[52] U.S. Cl. .......................... 606/86; 626/79; 626/87; 626/88; 626/75; 623/13; 606/69
[58] Field of Search ................ 606/79, 69, 83, 606/84, 85, 86, 87, 88, 96, 75; 623/13

[56] References Cited

U.S. PATENT DOCUMENTS

| | | | |
|---|---|---|---|
| 493,730 | 3/1893 | MacKenzie | 606/179 |
| 1,911,873 | 5/1933 | Balton | 83/86 |
| 2,573,462 | 10/1951 | Lindsey | 408/86 |
| 2,591,516 | 4/1952 | Darnell | 425/280 |
| 4,007,732 | 2/1977 | Kvavle et al. | 128/754 |
| 4,059,115 | 11/1977 | Jumashev et al. | 606/82 |
| 4,177,797 | 12/1979 | Baylis et al. | 128/754 |
| 4,649,918 | 3/1987 | Pegg et al. | 606/79 |
| 4,741,651 | 5/1988 | Despres | 408/209 |
| 4,782,833 | 11/1988 | Einhorn et al. | 606/80 |
| 4,913,143 | 4/1990 | Oloff et al. | 606/170 |
| 4,936,313 | 6/1990 | Burkhardt et al. | 128/751 |
| 5,139,520 | 8/1992 | Rosenberg | 623/13 |
| 5,152,763 | 10/1992 | Johnson | 606/86 |
| 5,197,967 | 3/1993 | Wilson | 606/79 |
| 5,211,647 | 5/1993 | Schmieding | 606/104 |
| 5,269,786 | 12/1993 | Morgan | 606/96 |
| 5,320,115 | 6/1994 | Kenne | 623/13 |
| 5,320,626 | 6/1994 | Schmieding | 606/96 |
| 5,423,823 | 6/1995 | Schmieding | 606/80 |
| 5,496,326 | 3/1996 | Johnson | 606/79 |
| 5,562,669 | 10/1996 | McGuire | 606/88 |
| 5,603,716 | 2/1997 | Morgan et al. | 606/88 |

OTHER PUBLICATIONS

M. Brittberg et al., "Treatment of Deep Cartilage Defects in the Knee with Autologous Chondrocyte Transplantation," *New England J. Med.*, vol. 331, No. 14, pp. 889-895 (Oct. 6, 1994).

V. Bobic, "Arthroscopic Osteochondral Autograft Transplantation in Chronic Anterior Cruciate Ligament Reconstruction," ESSKA 96, (1996).

V. Bobic, "An Update on Arthroscpoic Osteochondral Autograft Transplantation in ACL Reconstruction," AOSSM 22nd Annual Meeting, (1996).

V. Bobic, "Athroscropic Osteochondral Autograft Transplantation in Anterior Cruciate Ligament Reconstruction: A Preliminary Clinical Study," *J Bone Joint Surgery* [BR], vol. 78-B: Supp. 1 (1996).

Mankin et al., Restoration of the Osteoarthrotic Joint, *J Bone Joint Surgery*, vol. 78-A, No. 1, pp. 1-2 (Jan. 1996).

J. Buckwalter, "New Methods of Treating Chondral Defects in the Knee" (undated).

L. Hangody, "Autologous Osteochondral Mosaic–Like Graft Technique for Replacing Weight–Bearing Cartilage Defects," ESSKA 96, Budapest, Hungary, (May 10-15, 1996).

(List continued on next page.)

*Primary Examiner*—Michael Powell Buiz
*Assistant Examiner*—Daphna Shai
*Attorney, Agent, or Firm*—Ostrolenk, Faber, Gerb & Soffen, LLP

[57] ABSTRACT

A method of reconstructing the anterior cruciate ligament using arthroscopic surgery. A closed-ended socket is formed in the tibia and the femur. The locations of the sockets are determined using an offset aimer to reference anatomical structures within the knee. An ACL graft is fixated in the tibial and femoral sockets using interference screws. The method obviates the need to form tibial incisions and tunnels, as required by existing methods.

12 Claims, 14 Drawing Sheets

OTHER PUBLICATIONS

N. Gould, "Trephining Your Way," *Orthopedic Clinics of North America*, vol. 4, No. 1, pp. 157–164 (Jan. 1973).

V. Bobic, "Arthroscopic osteochondral autograft transplantation in anterior cruciate ligament reconstruction: a preliminary clinical study," *Knee Surg. Sports Traumatol. Athroscopy*, vol. 3, pp. 262–264 (1996).

L. Hangody et al., "MosaicPlasty™ Osteochondral Grafting Technique Guide," Smith & Nephew Endoscopy brochure (1996).

C. Fabbriciani et al., "Osteochondral Autograft in the Treatment of O.D. of the Knee," Orthopaedic Clinic, Catholic Univ., Rome, Italy (1996).

Y. Matsusue, "Arthroscopic Multiple Osteochondral Transplantation to the Chondral Defect in the Knee Associated with Anterior Cruciate Ligament Disruption," *Arthroscopy*, 9(3), pp. 318–321 (1993).

F. Yamashita, "The Transplantation of an Autogeneic Osteochondral Fragment for Osteochrondrtis Dissecans of the Knee," *Clinical Orthopaedics*, No. 201, pp. 43–50 (Dec. 1985).

METHOD OF ACL RECONSTRUCTION USING DOUBLE SOCKET GRAFT PLACEMENT AND FIXATION

BACKGROUND OF THE INVENTION

1. Field of the Invention

The present invention relates to a method of reconstructive knee surgery, and more specifically to a method for arthroscopic reconstruction of the anterior cruciate ligament (ACL).

2. Description of the Related Art

An existing preferred method of ACL reconstruction, described in U.S. Pat. Nos. 5,211,647 and 5,320,626, involves drilling a tunnel through the tibia, drilling a closed tunnel (socket) into the femur, inserting a substitute ACL graft from one tunnel to the other, and securing the respective ends of the graft to the walls of the tibial and femoral tunnels using interference screws or the like. Accurate positioning of the tibial and femoral tunnels requires a drill guide, such as disclosed in U.S. Pat. Nos. 5,269,786 and 5,350,383. Additionally, a tibial incision is required for creating and accessing the tibial tunnel.

Although the existing method of ACL reconstruction described above is superior to prior techniques of ACL reconstruction and is now widely practiced, it nevertheless has a number of attendant disadvantages: (1) the drill guide is cumbersome; (2) the creation of the tibial tunnel with the use of the drill guide involves removing a considerable amount of bone; and (3) the tibial incision opened is relatively large and obtrusive. Accordingly, a need exists for a simpler, less obtrusive method of ACL reconstruction.

SUMMARY OF THE INVENTION

The present invention is a method of ACL reconstruction that advantageously eliminates the need for a tibial tunnel and a tibial incision. The present invention thus advantageously simplifies ACL reconstruction and reduces morbidity associated with creating the tibial incision and tibial tunnel.

The present invention avoids the need for a tibial tunnel by positioning and securing the ends of a ligament graft in a patient's knee in closed-ended sockets formed in the tibia and femur. Specifically, in accordance with the present invention, a socket is formed in the tibia, a socket is formed in the femur, the first end of the graft is inserted into the femoral socket, the second end of the graft is inserted into the tibial socket, the second end of the graft is secured in the tibial socket, and the first end of the graft is secured after tensioning in the femoral socket.

The tibial socket is preferably formed by:

(i) forming a portal in the knee, preferably at a position superomedial to the patella; (ii) inserting an offset aimer having a cannulated shaft and an offset hook located on a distal end thereof through the portal and referencing the anterior margin of the PCL with the offset hook; (iii) inserting a drill pin through the cannulated shaft of the offset aimer to mark a position in the tibia on the intercondylar floor for creating the tibial socket at a point sagittally central in the original ACL origin; and (iv) creating the tibial socket at the marked position. The femoral socket is formed similarly, but through an anterior medial portal, using the offset hook positioned "over the top" in the posterior intercondylar notch in the femur for positioning and creating the femoral socket in the original ACL origin.

To create each of the sockets, a hole is formed in the bones (the tibia or femur) at the position marked by the offset hook.

A collared pin is inserted into the hole. A bone harvester, in the form of a cannulated, sharp-ended coring device, is placed over the collared pin for centering and directional control. The bone harvester is impact-driven into the bone at the marked location. As the harvester is advanced to a desired depth, it collects bone material, forming a bone core. The bone harvester and the bone core contained therein are then removed from the bone by retrograding the tool, leaving a socket in the bone. Following removal of the harvester from the knee, the bone core is removed from within the bone harvester by tapping on the collared pin.

The insertion and fixation of the graft within the femoral and tibial sockets is preferably performed by attaching the graft with suture to a drill pin with a threaded eye, inserting the graft into the knee using the drill pin with a threaded eye as a guide, using the drill pin with a threaded eye to pull the first end of the graft from the anteromedial portal into the femoral socket, inserting a first bone block into the femoral socket to wedge the first end of the graft against a wall of the femoral socket, inserting the second end of the graft into the tibial socket, inserting a second bone block into the tibial socket to wedge the second end of the graft against a wall of the tibial socket, securing the second end of the graft into the tibial socket by interference screw fixation, and securing the first end of the graft into the femoral socket by interference screw fixation after tensioning the graft by pulling on the graft-passing sutures on the femoral side.

If a semitendinosus graft is used for the ACL reconstruction, the harvested bone cores can be used to form the bone blocks for fixation of the graft, as described in U.S. Pat. No. 5,397,357, issued Mar. 14, 1995, the disclosure of which is incorporated herein by reference.

Other features and advantages of the present invention will become apparent from the following description of the invention which refers to the accompanying drawings.

DETAILED DESCRIPTION OF THE PREFERRED EMBODIMENT

Figure 1:
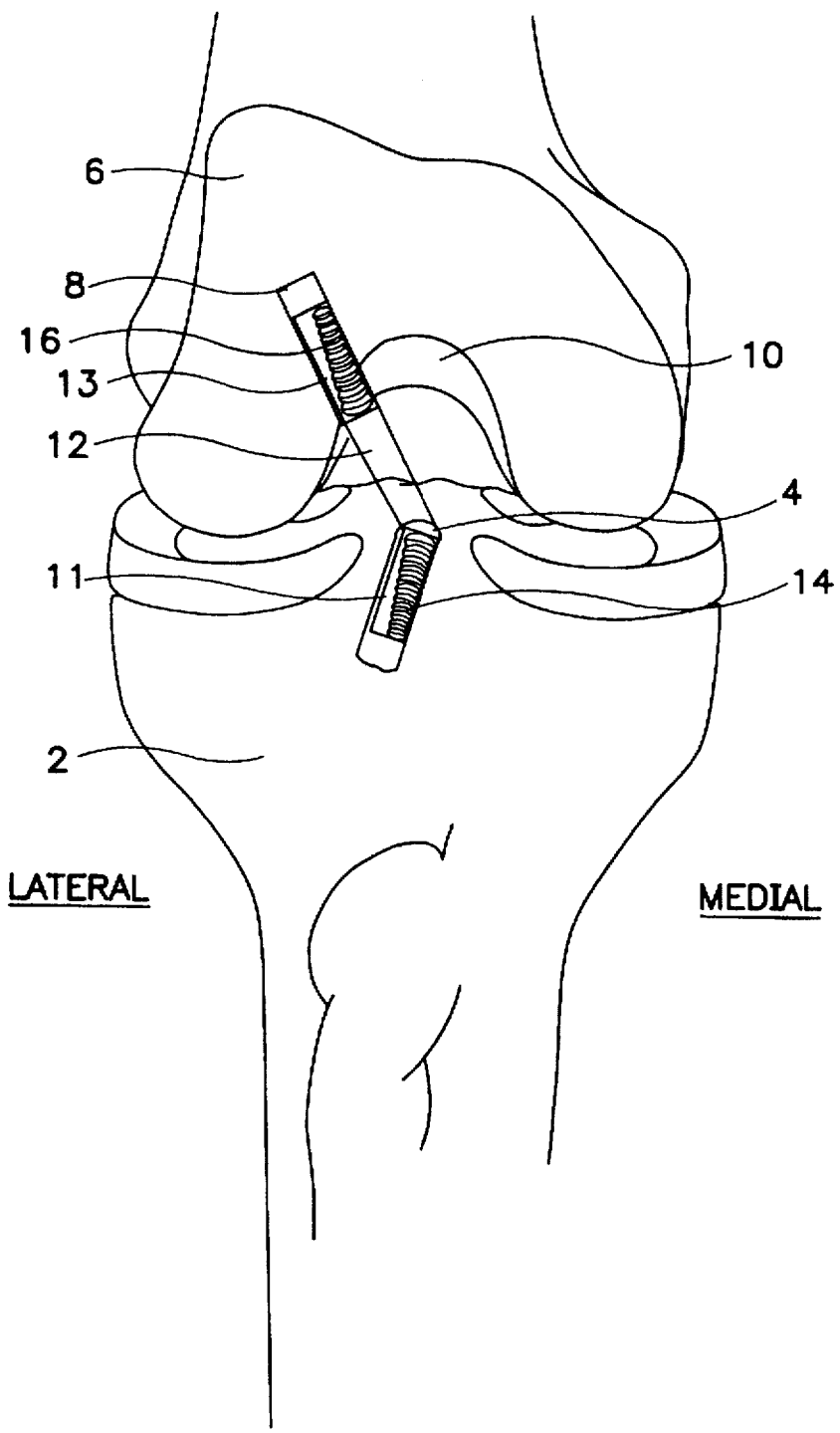
FIG. 1 is an interior view of the knee showing an ACL graft reconstruction according to a preferred embodiment of the method of the present invention.

A preferred method of ACL reconstruction is now described, with reference to the drawings, as follows:

FIG. 1 is a schematic, anterior view of a knee in which an ACL reconstruction has been performed in accordance with the method of the present invention. A tibia 2 has a tibial socket 4 formed therein, and femur 6 has a femoral socket 8 formed similarly near the intercondylar notch 10. A bone block 11 at one end of an ACL graft 12 is secured in tibial socket 4 by an interference screw 14. At the opposite end of ACL graft 12, bone block 13 is secured in femoral socket 8 by an interference screw 16.

Figure 2:
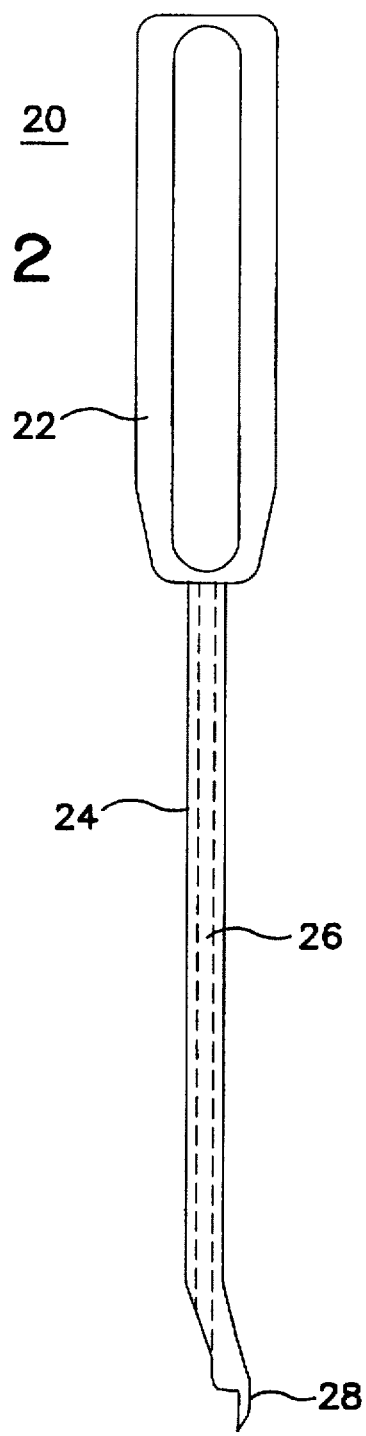
FIG. 2 is a side view of a 7 mm offset aimer used in performing an ACL reconstruction according to a preferred embodiment of the present invention.

FIGS. 2–5 illustrate various instruments used in the method of the present invention, as described more fully below. FIG. 2 shows a cannulated, offset aimer 20, similar to the instrument described and claimed in U.S. Pat. No. 5,320,626, herein incorporated by reference. The offset aimer includes handle 22, located at a proximal end of the aimer, and a shaft 24 connected to the handle. Shaft 24 is hollow, forming a cannula 26 for receiving a guide pin. An offset tip 28 is provided at a distal end of aimer 20. In the preferred embodiment of the present invention, tip 28 is configured to provide a 7 mm offset from a referencing point, as described in further detail below.

Figure 3:
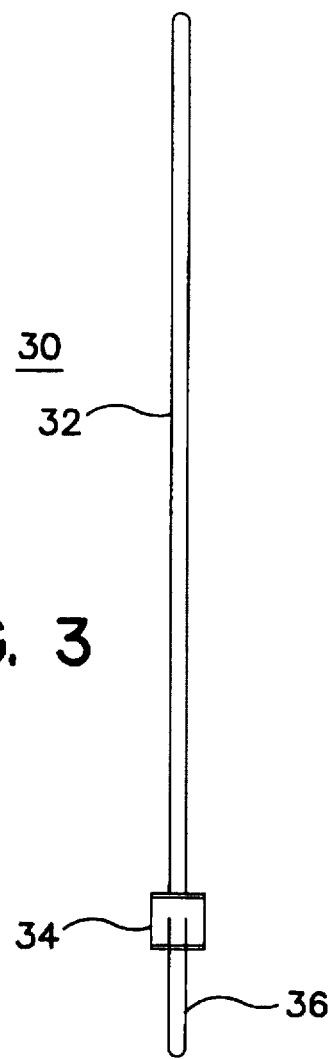
FIG. 3 is a side view of a collared guide pin used in performing an ACL reconstruction according to a preferred embodiment of the present invention.

FIG. 3 shows a collared pin 30 used in the method of the present invention. Collared pin 30 has a shaft 32 with a collar 34 located near a distal end of the shaft. Collared pin 30 has a distal end 36 that extends beyond collar 34.

Figure 4:
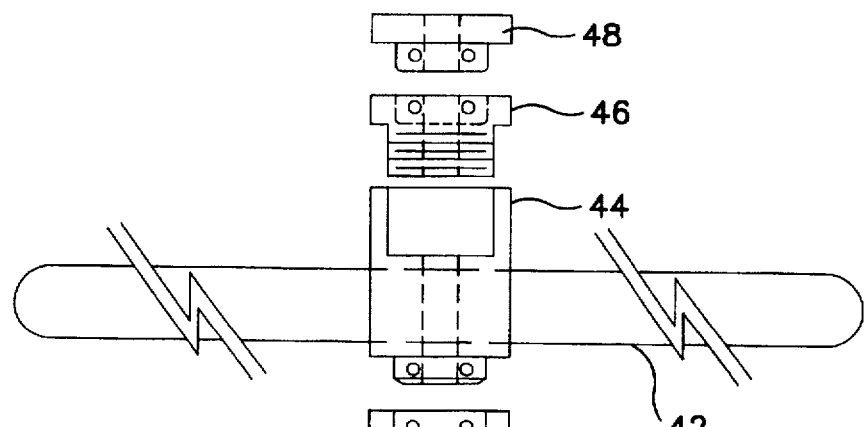
FIG. 4 is a side view of a keyless hand chuck used in performing a method of ACL reconstruction according to a preferred embodiment of the present invention.

FIG. 4 shows a keyless, cannulated chuck 40 used in the invention, as described below. Keyless chuck 40 includes a "T" rod 42 inserted through a handle 44. Chuck 40 has a threaded end piece 46 and a removable end cap 48 located on a distal end of the chuck.

Figure 5:
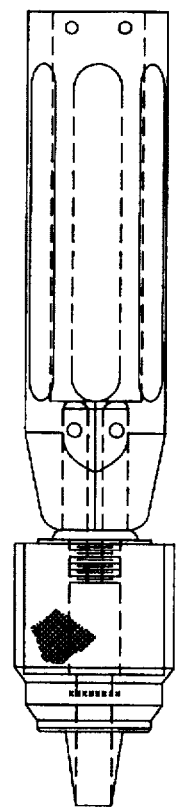
FIG. 5 is a side view of a bone harvester used in performing a method of ACL reconstruction according to a preferred embodiment of the present invention.

FIG. 5 shows a bone harvester 50 used to remove a bone core in the present invention. Harvester 50 is a sharp-ended coring device which includes a shaft 52 with a cannula 54 for receiving the bone core. Shaft 52 opens into a hollow tube 56 with a tapered back end 58.

Figure 6:
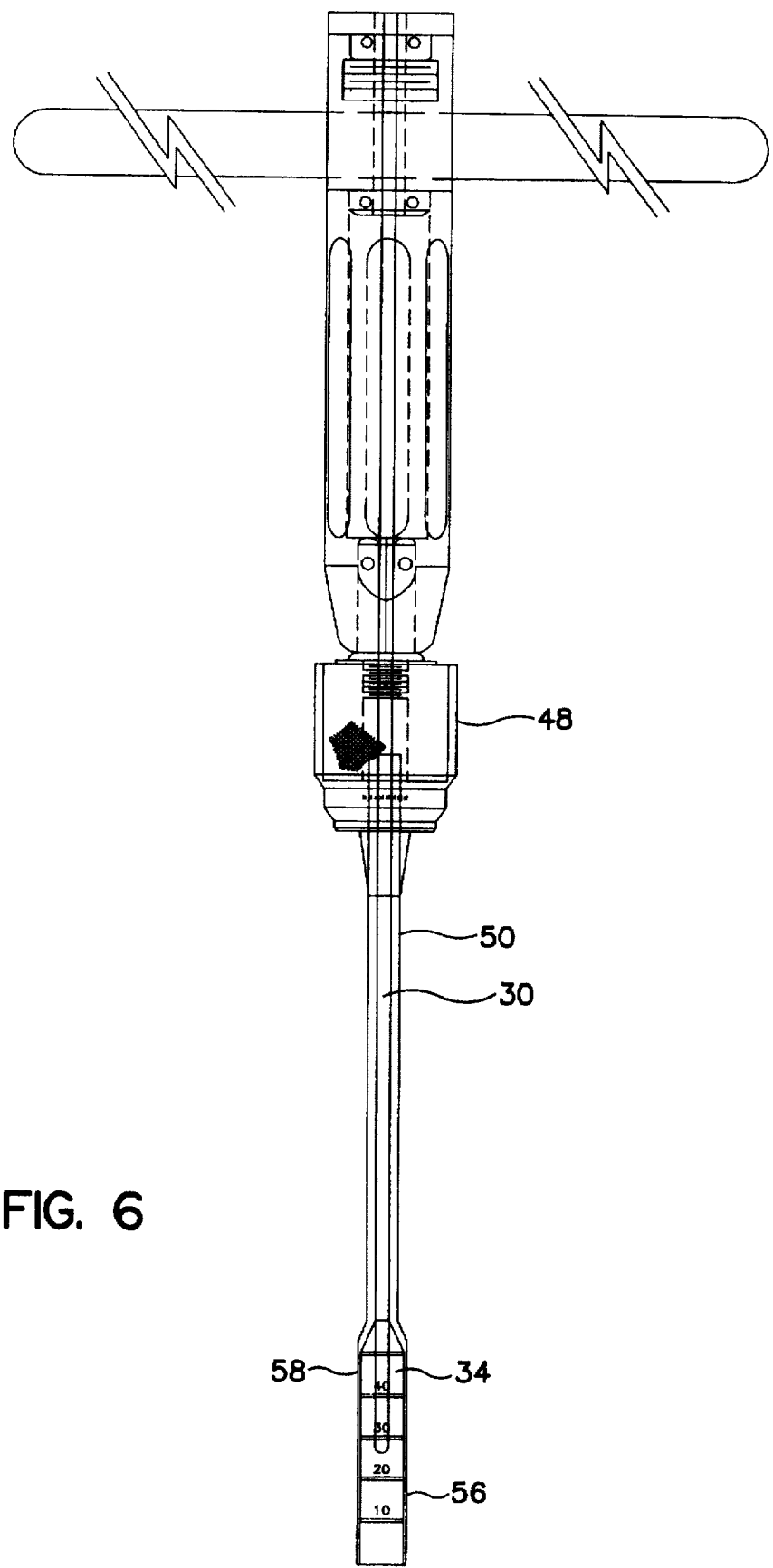
FIG. 6 is an assembly view of the bone harvester of FIG. 5 inserted in the hand chuck of FIG. 4 and surrounding the collared guide pin of FIG. 3.
Figure 7:
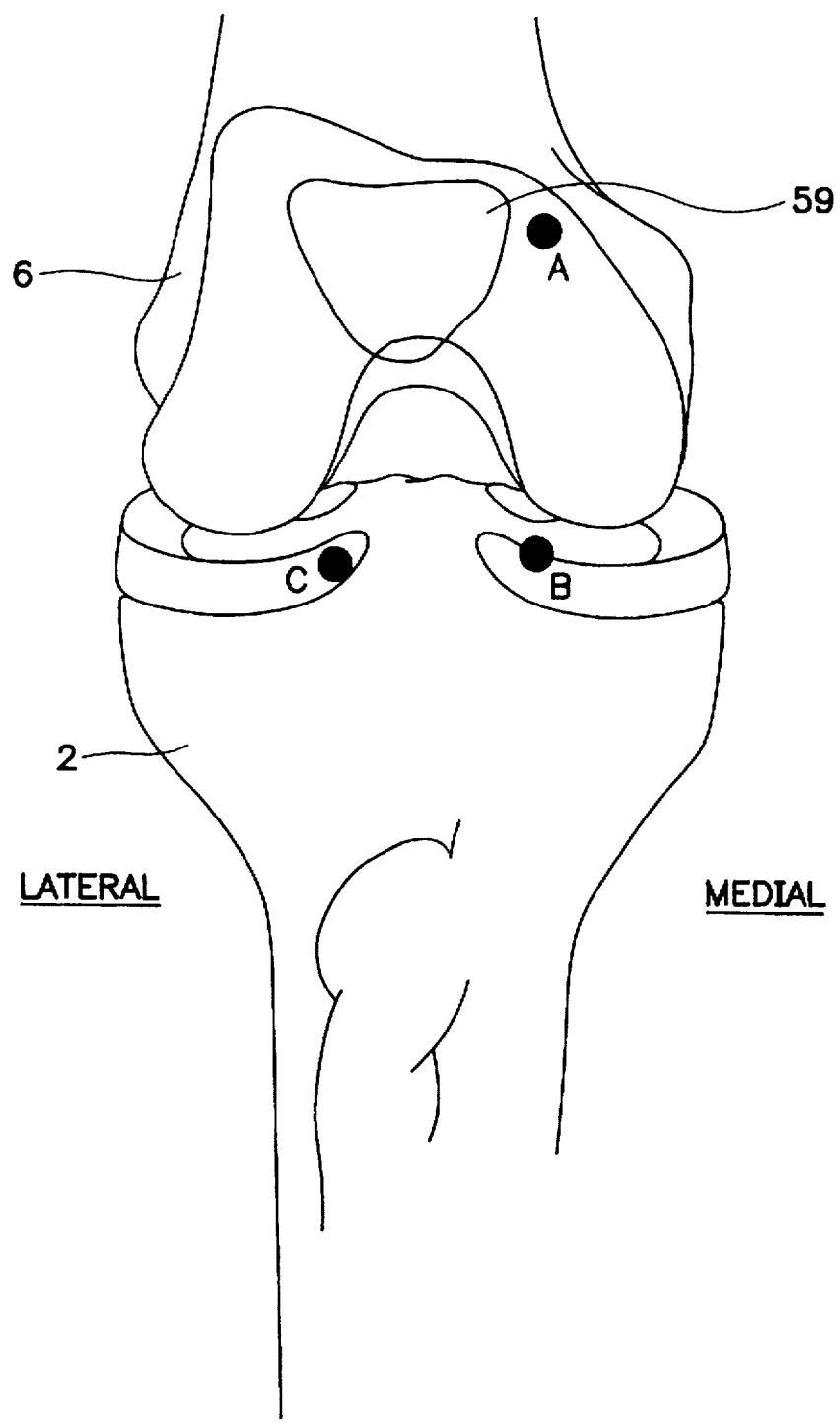
FIG. 7 is an anterior view of the knee indicating the location of arthroscopic portals used in performing a method of ACL reconstruction according to a preferred embodiment of the present invention.

As shown in FIG. 6, bone harvester 50 is adapted to be inserted over collared pin 30 and received in chuck 40. Shaft 32 of collared guide pin 30 is inserted within cannula 46 of keyless chuck 40 and extends through cannula 54 of bone harvester 50.

The method of ACL reconstruction according to a preferred embodiment of the present invention is now described with reference to FIGS. 7–16 as follows:

The first step of the method is the formation of portals for arthroscopic surgery. A portal A medial to a superior patella 59 is formed, at the position shown schematically in the anterior view of the knee of FIG. 7. Anteromedial portal B and anterolateral portal C are also formed for inserting a 30-degree arthroscope and other instruments, as described below.

Figure 8:
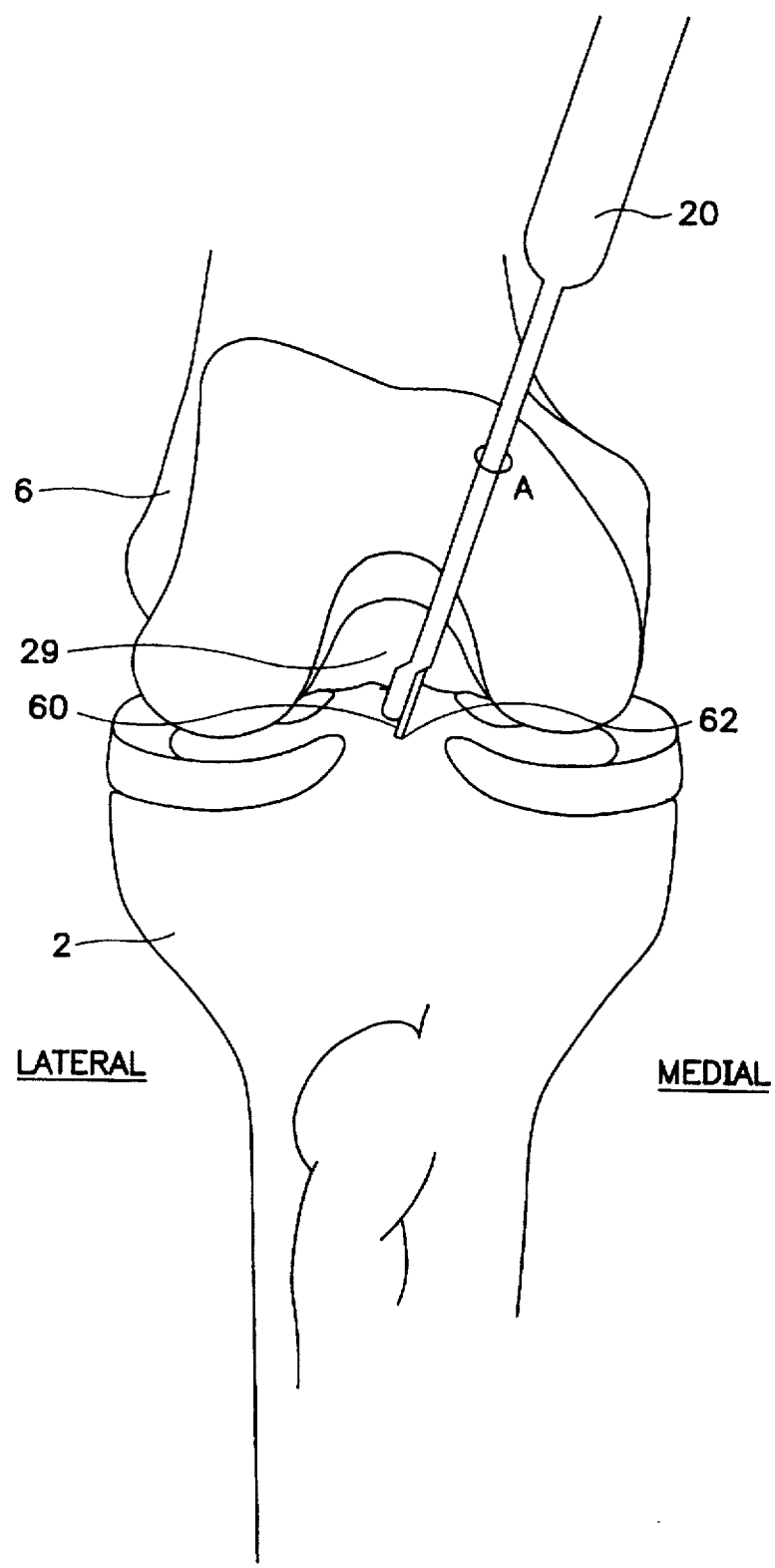
FIG. 8 is an anterior view of the knee indicating the placement of the offset aimer of FIG. 2, as used in forming a tibial socket for performing a method of ACL reconstruction according to a preferred embodiment of the present invention.

Referring now to FIG. 8, offset aimer 20 is inserted into portal A to mark the location of the tibial socket for the ACL graft. The backside surface of tip 28 is brought into contact with the anterior margin of the posterior cruciate ligament (PCL) 29, whereby the central axis of cannula 26 is offset 7 mm from the anterior margin of the PCL. Tip 28 preferably has a pointed end for anchoring the instrument into the intercondylar floor. A drill pin 60 is inserted through cannula 26 of offset aimer 20 (FIG. 2). A hole 62 is drilled with pin 60 into the intercondylar floor of the tibia in a proper location for the tibial tunnel 4, i.e. at a point sagittally central in the original ACL origin, as shown in FIG. 1.

Figure 9:
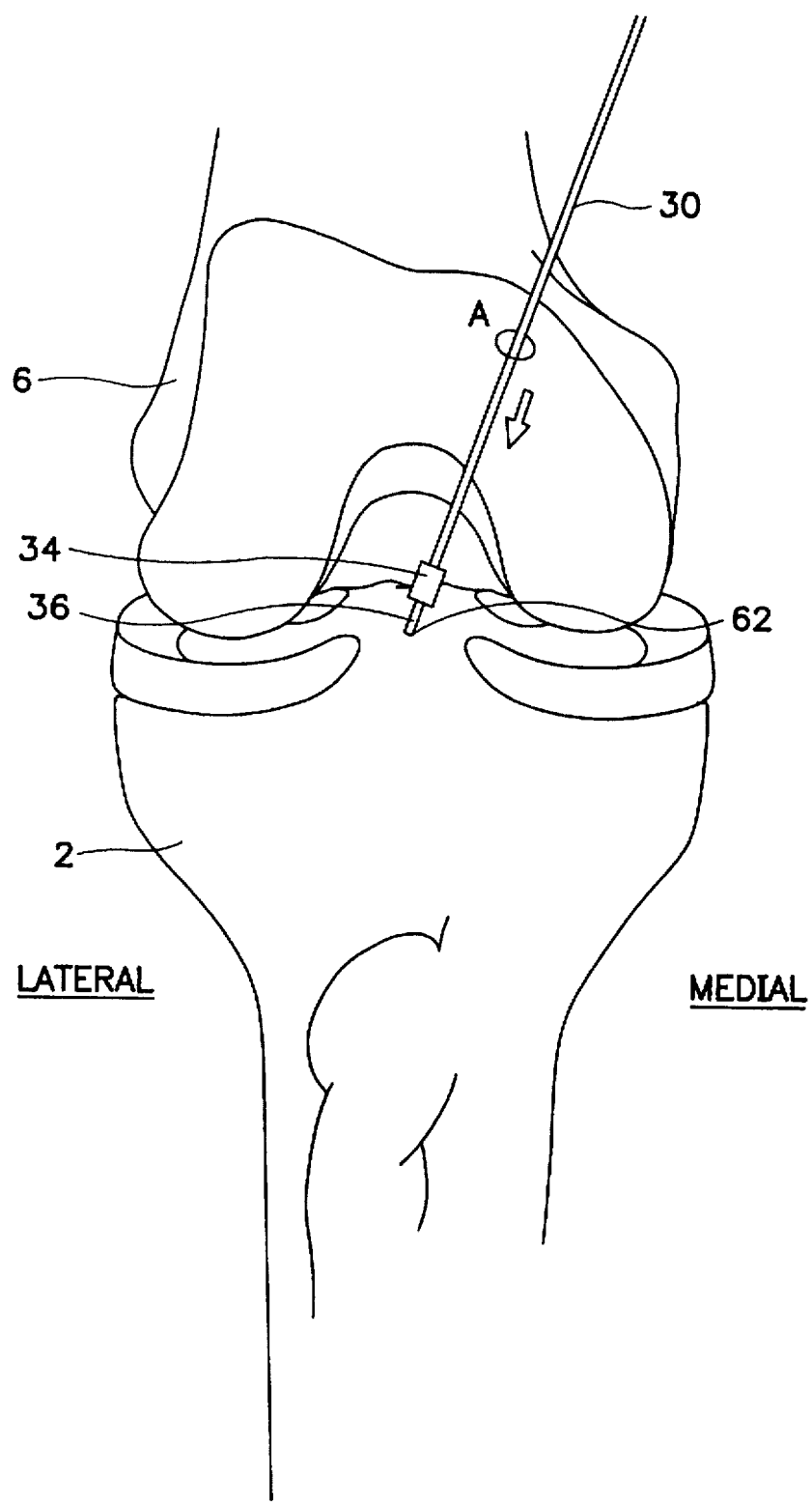
FIG. 9 is an anterior view of the knee indicating the placement of the collared guide pin of FIG. 3 as used in forming a tibial socket for performing a method of ACL reconstruction according to a preferred embodiment of the present invention.

Referring now to FIG. 9, offset aimer 20 and drill pin 60 are then removed, and distal end 36 of collared pin 30 is inserted into the drill hole 62, in the direction of the arrow, as shown.

Figure 10:
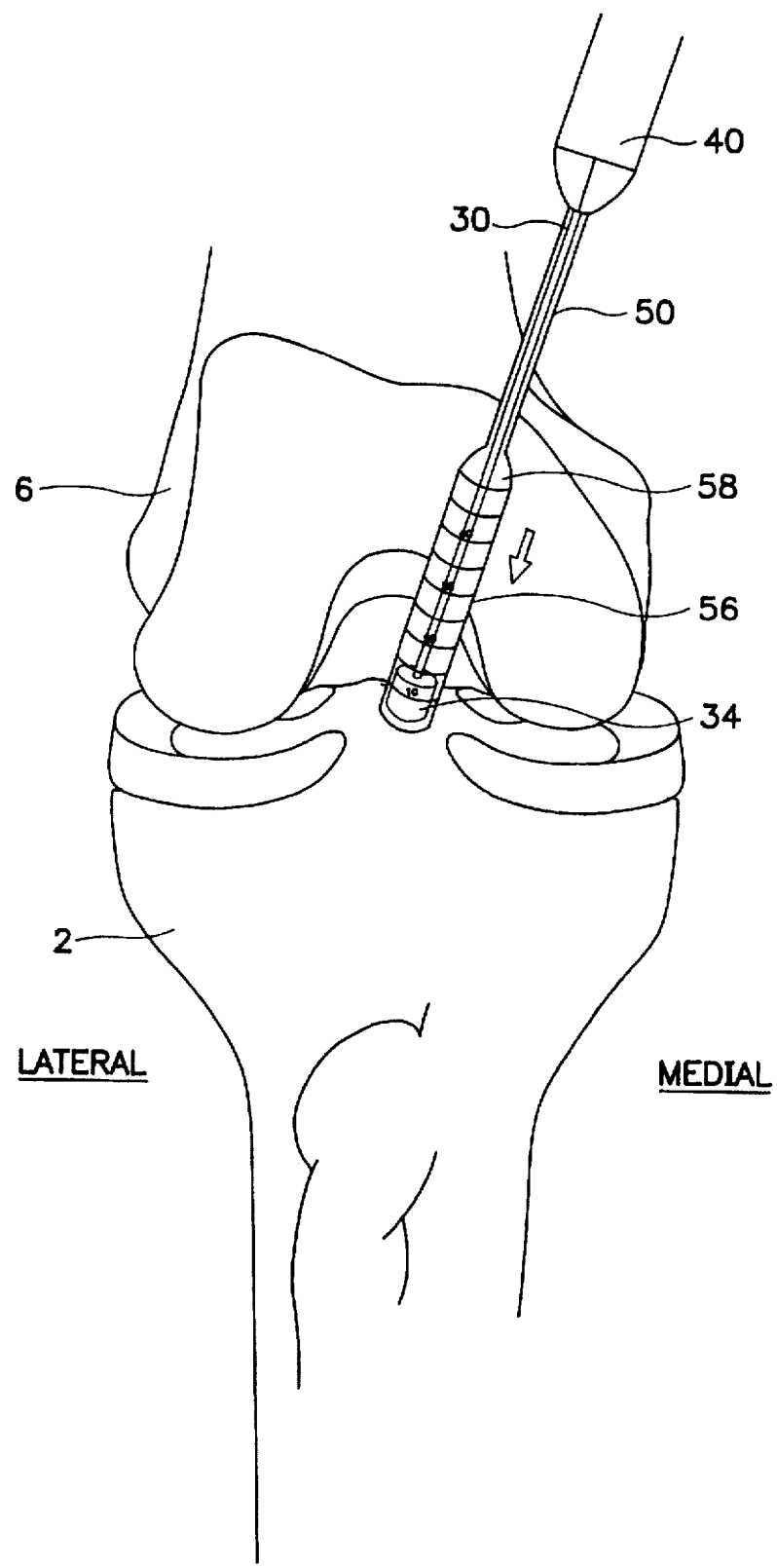
FIG. 10 is an anterior view of the knee indicating the placement of the bone harvester used in forming a tibial socket for performing a method of ACL reconstruction according to a preferred embodiment of the present invention.

Next, the proximal end of bone harvester 50 is installed into keyless chuck 40 (as shown in the assembly drawing of FIG. 6). Referring to FIG. 10, the distal end of the harvester 50 is inserted into the knee and slid over collared pin 30 for centering and directional control. The proximal end of keyless chuck 40 is then impacted until harvester 50 is driven to a desired depth into the tibia. Depth calibration markings, located on the side of tube 56, aid in determining depth. Ordinarily, the harvester will be driven to a depth of about 25 to 30 mm. As a safeguard, when harvester 50 reaches a maximum depth of 40 mm, collar 34 becomes seated in back end 58 of tube 56, preventing further insertion of the harvester. Maximum insertion of the harvester also will be indicated to the surgeon visually when a distal end of collared guide pin 30 comes flush with removable end cap 48 at the proximal end of keyless chuck 40.

As a result of impacting, bone material collects within tube 46 of harvester 40, forming a tibial bone core. Using T-rod 42 on keyless chuck 40, bone harvester 50 is twisted to break the tibial bone core loose from tibial bone socket 4. The tibial bone core is then extracted from the bone socket and the knee with bone harvester 40 by using a simultaneous twisting and pulling motion.

After extraction of the bone core, end cap 48 of the keyless chuck is removed to expose the distal end of collared guide pin 30. Impacting the collared guide pin pushes the bone core out of the bone harvester.

Figure 11:
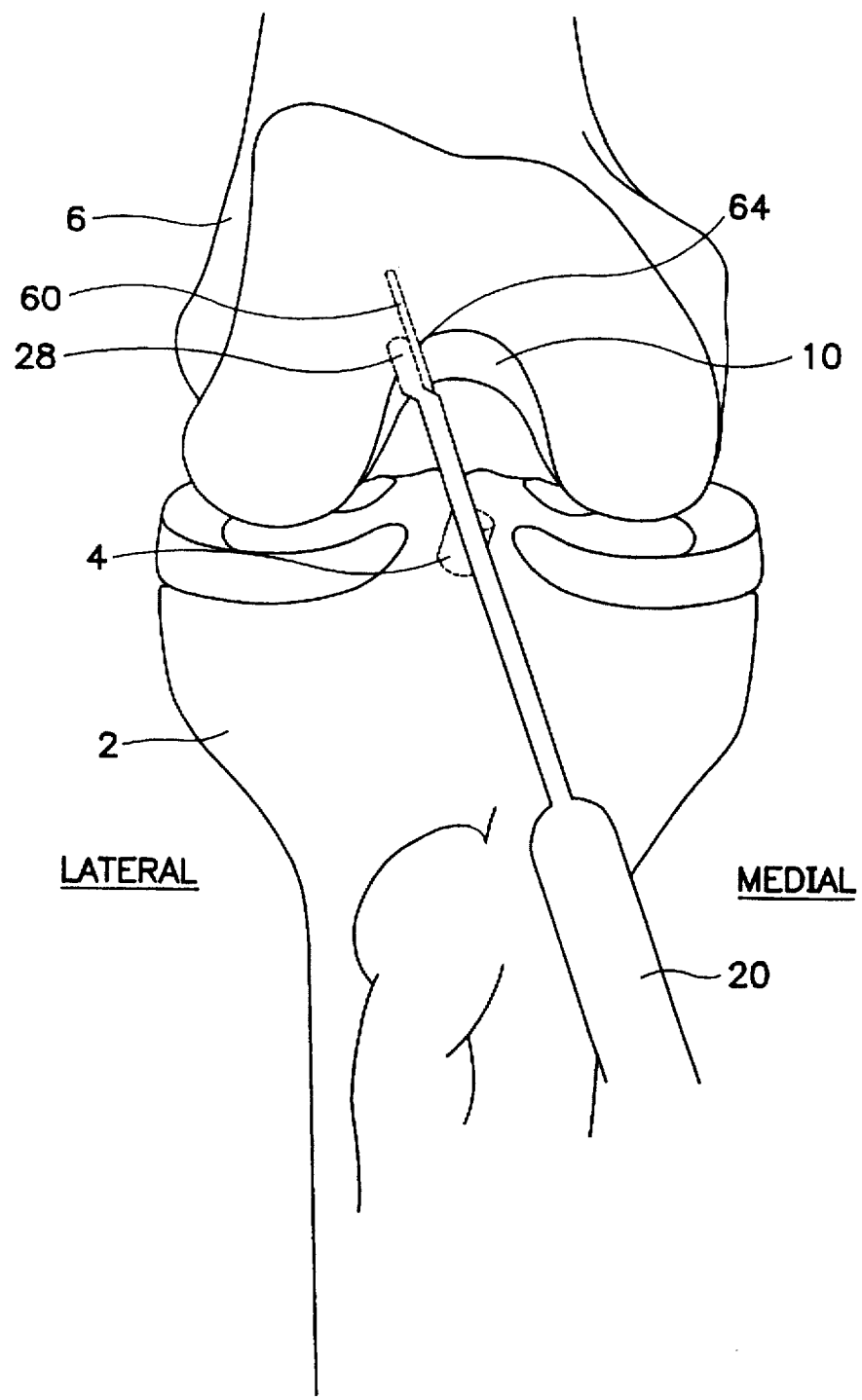
FIG. 11 is an anterior view of the knee indicating the placement of a drill pin within an offset aimer for creating a femoral socket according to a preferred embodiment of the present invention.

Referring now to FIG. 11, a procedure similar to that set forth above is used to form a femoral bone socket. Using offset aimer 20 to reference the intercondylar notch 10 (in a manner similar to that disclosed in U.S. Pat. No. 5,320,626), an over-the-top position of the posterior intercondylar notch is located and a femoral hole 64 is created, using pin 60, through anterior medial portal B.

Figure 12:
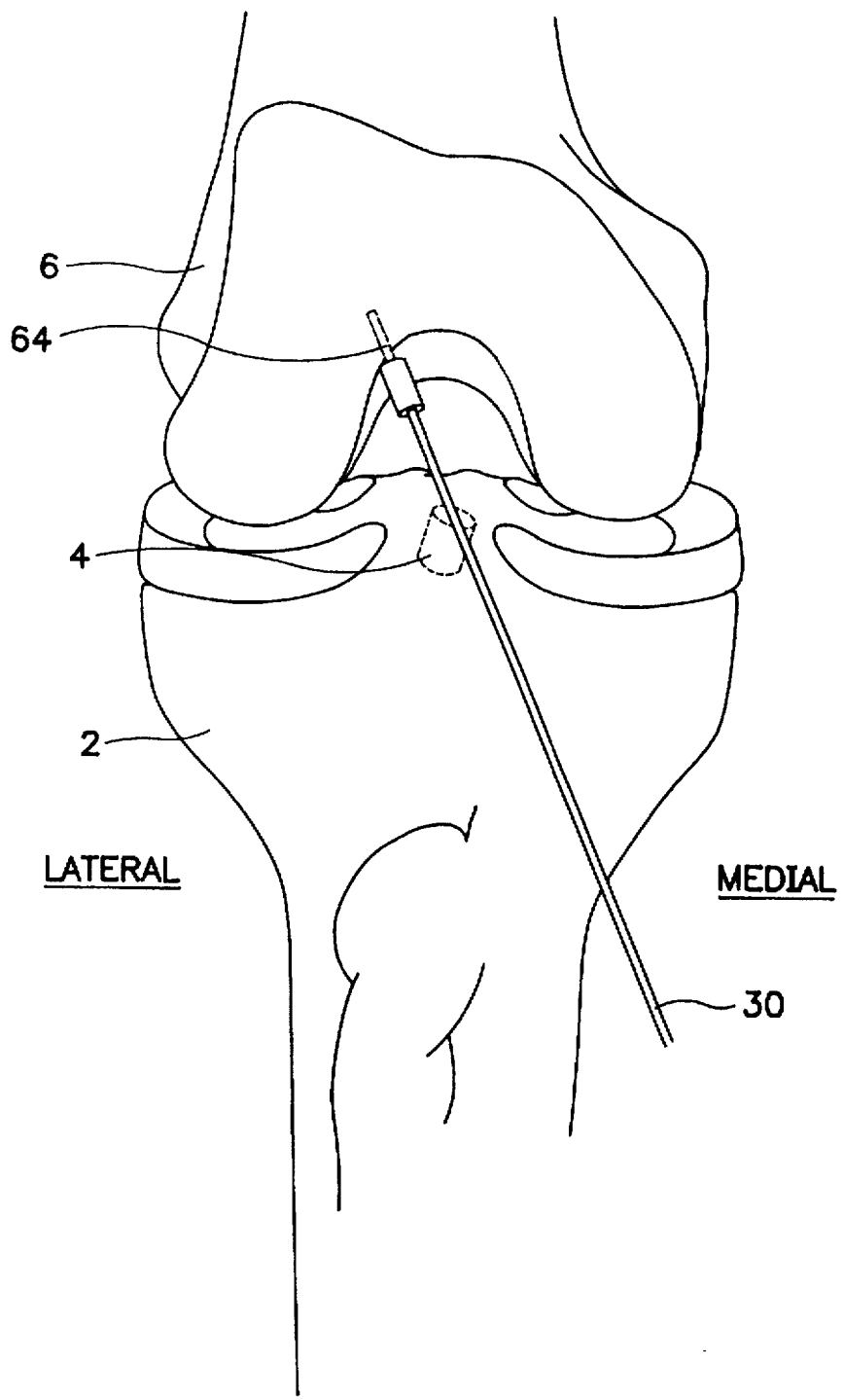
FIG. 12 is an anterior view of the knee showing the femoral placement of the collared pin used in performing a method of ACL reconstruction according to a preferred embodiment of the present invention.
Figure 13:
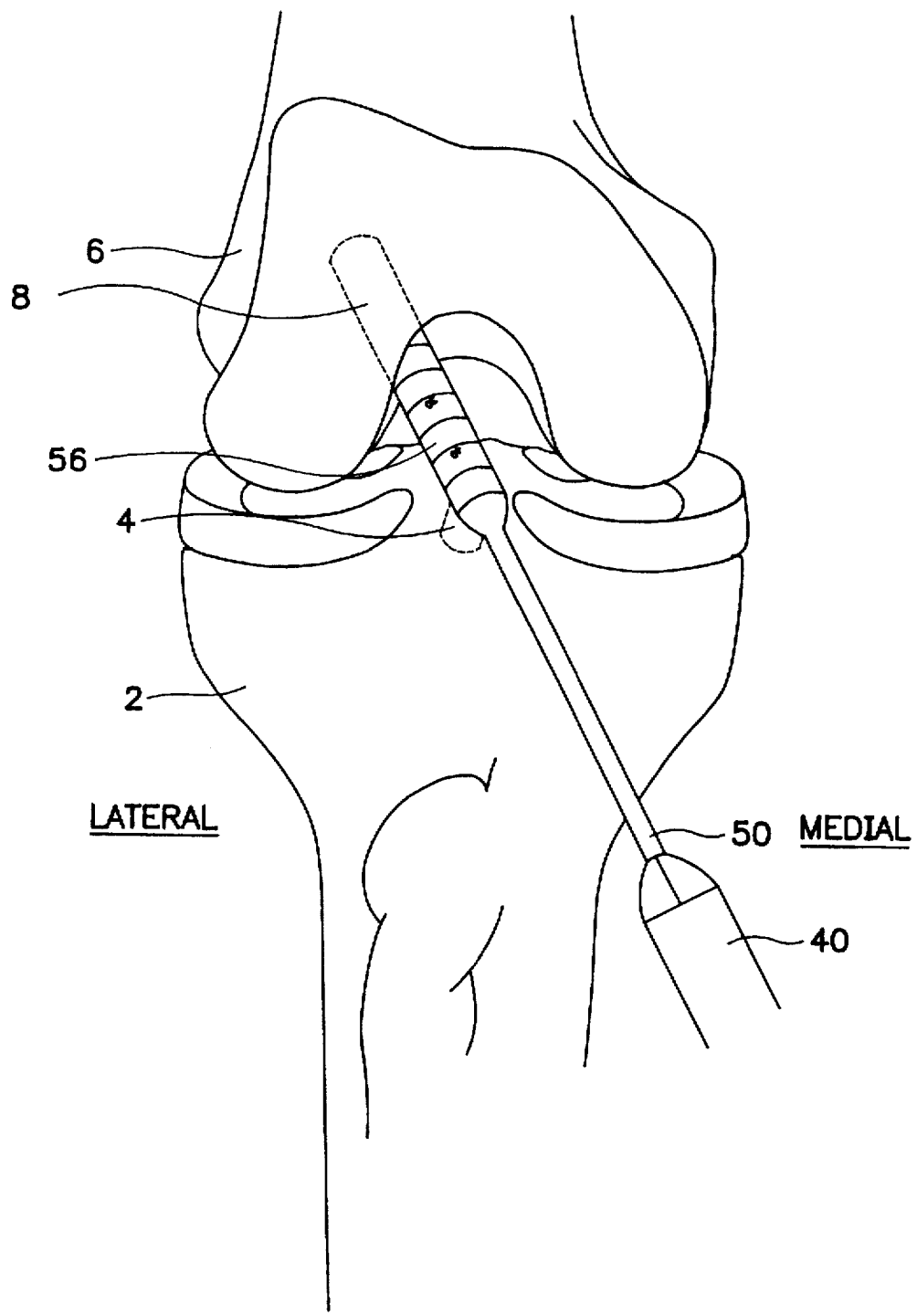
FIG. 13 is an anterior view of the knee showing the femoral placement of the bone harvester used in performing a method of ACL reconstruction according to a preferred embodiment of the present invention.

Next, as shown in FIG. 12, pin 60 is replaced with collared pin 30, which is inserted in femoral hole 64, in a manner similar to that described above with respect to tibial hole 62. Referring to FIG. 13, bone extractor 50 is impacted to an appropriate femoral depth to form a femoral bone core and femoral socket 8, in a manner analogous to that described above with respect to tibial bone core and socket formation.

Figure 14:
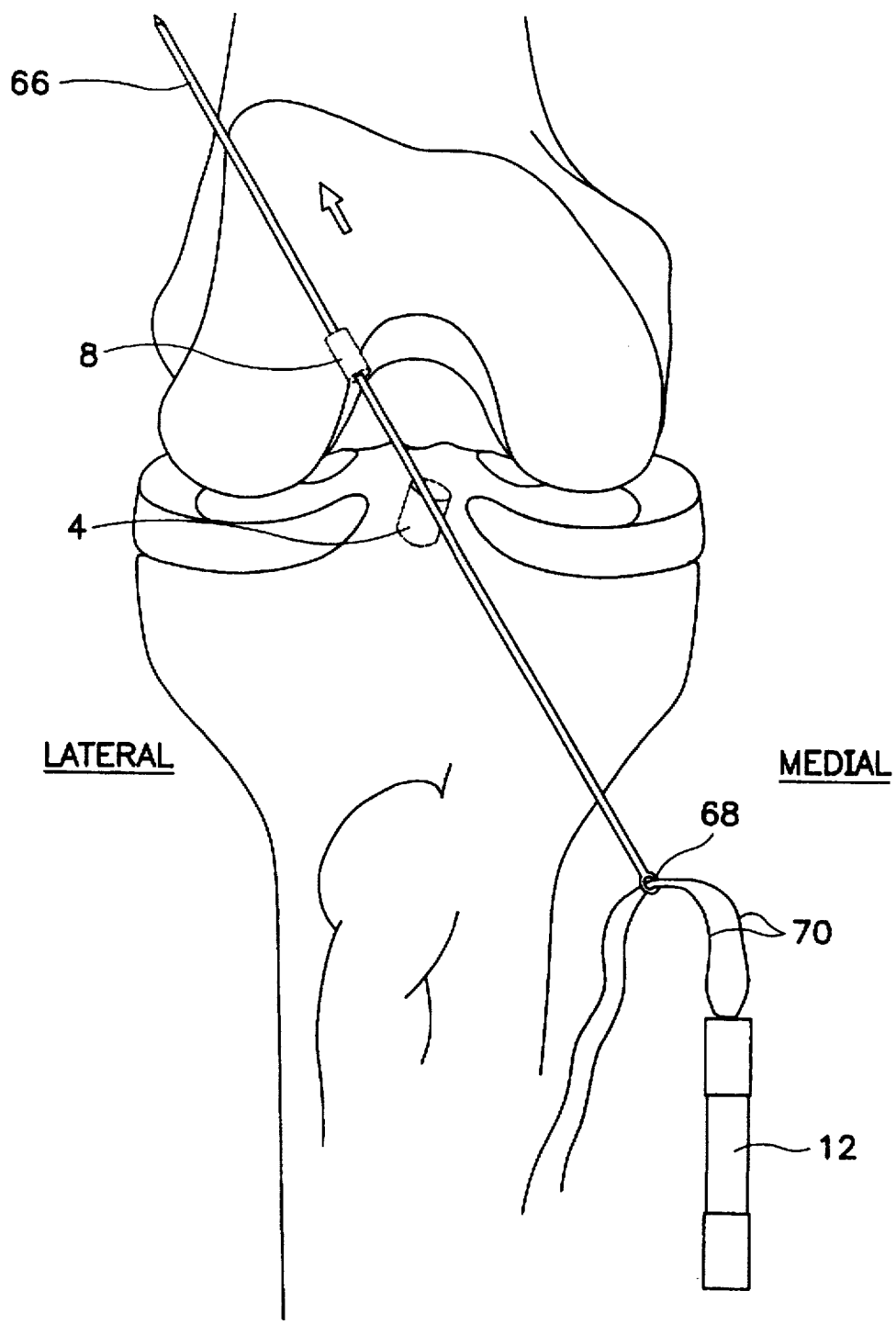
FIG. 14 is an anterior view of the knee showing the femoral insertion of a suture pin threaded with an ACL graft used in performing a method of ACL reconstruction according to a preferred embodiment of the present invention.

Referring now to FIG. 14, a drill pin 66 with a suture eye 68 is drilled through anterior medial portal B into femoral socket 8 until drill pin exits the lateral thigh. The ACL graft 12 is attached to the suture eye of the pin using graft passing sutures 70 and the graft is pulled from the anteromedial portal B into the femoral socket. A probe or grasper (not shown) is used to aid insertion and to orient the graft.

Figure 15:
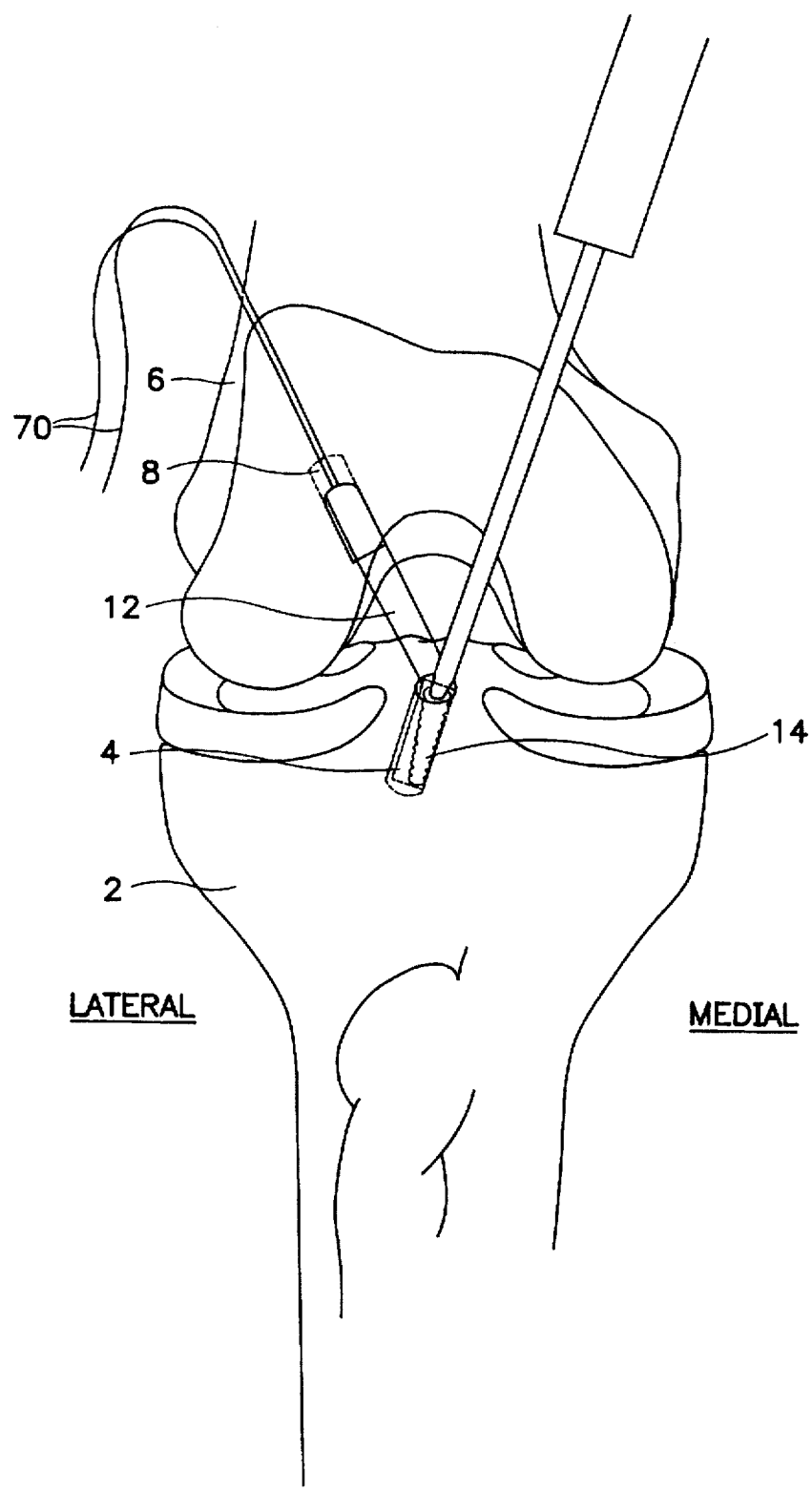
FIG. 15 is an anterior view of the knee showing tibial insertion of an interference screw used in performing a method of ACL reconstruction according to a preferred embodiment of the present invention.

Using the grasper, the tibial end of graft 12 is properly positioned and inserted into tibial socket 4. Referring to FIG. 15, the tibial end of graft 12 is fixated into tibial socket 4 using interference screw 14 inserted through superior-medial portal A.

Figure 16:
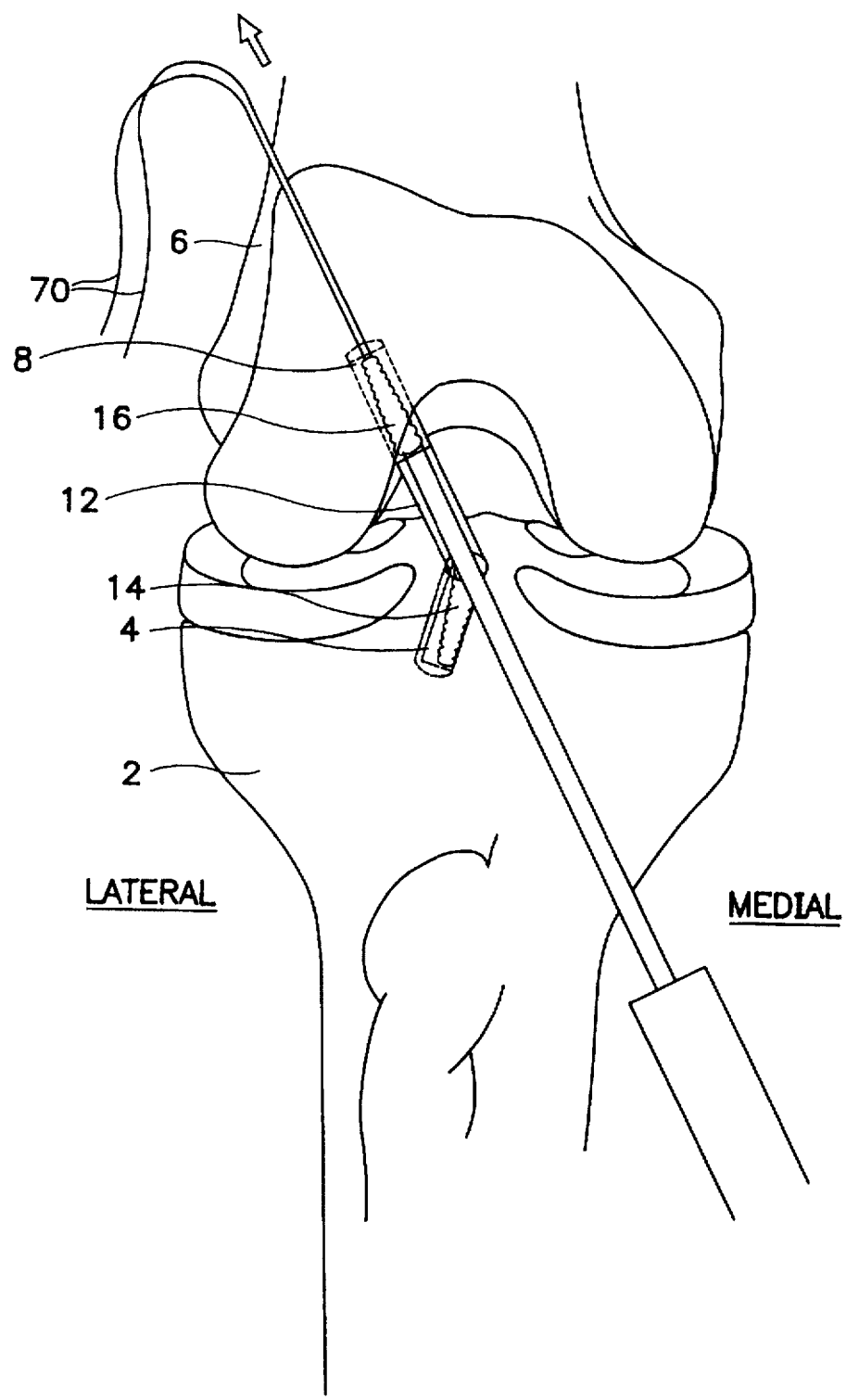
FIG. 16 is an anterior view of the knee showing tibial insertion of an interference screw used in performing a method of ACL reconstruction according to a preferred embodiment of the present invention.

Similarly, with reference to FIG. 16, after tensioning the graft by pulling on the graft-passing sutures 70 on the femoral side, an interference screw 16 is inserted into femoral tunnel 8 through the anterior medial portal B to fixate the femoral end of graft 12, completing the procedure of the present invention.

If a semitendinosus graft is used for the ACL reconstruction, the bone cores harvested from the femur and tibia can be used to form the bone blocks for fixation of the graft.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A surgical method for arthroscopic knee repair, comprising the steps of:
   (a) forming a portal in the knee;
   (b) forming a first closed-ended socket in the knee by inserting a bone harvester through the portal and driving the bone harvester into a bone in the knee, the bone harvester collecting bone material forming a bone core as the harvester is driven into the bone;
   (c) removing the bone harvester and the bone core contained therein;
   (d) forming a second closed-ended socket in the knee so as to produce a second bone core; and
   (e) inserting into at least one of the sockets at least a portion of one of the harvested bone cores.

2. A surgical method for arthroscopic knee repair as recited in claim 1, wherein said second closed-ended socket in the knee is formed by:
   (i) inserting a bone harvester into the knee and driving the bone harvester into bone in the knee at a location different from said first socket, the bone harvester collecting bone material forming a bone core as the harvester is driven into the bone; and
   (ii) removing the bone harvester and the bone core contained therein.

3. The method of claim 2, wherein the bone harvester is driven by impaction.

4. The method of claim 2, wherein the step of removing the bone harvester and the bone core comprises retrograding the bone harvester from the bone.

5. The method of claim 1, wherein the bone harvester is driven by impaction.

6. The method of claim 1, wherein the step of removing the bone harvester and the bone core comprises retrograding the bone harvester from the bone.

7. A surgical method for arthroscopic knee repair, comprising the steps of:
   (a) forming a portal in the knee;
   (b) forming a first closed-ended socket in the knee by inserting a bone harvester through the portal and driving the bone harvester into a first intercondylar surface of a bone in the knee, the bone harvester collecting bone material forming a first bone core as the harvester is driven into the bone;
   (c) removing the bone harvester and the first bone core contained therein;
   (d) forming a second closed-ended socket in the knee; and
   (e) inserting into at least one of the closed-ended sockets at least a portion of the harvested bone core.

8. A surgical method for arthroscopic knee repair as recited in claim 7, wherein said second closed-ended socket in the knee is formed by:
   (i) inserting a bone harvester into the knee and driving the bone harvester into a second intercondylar surface of a bone in the knee, the bone harvester collecting bone material forming a second bone core as the harvester is driven into the bone; and
   (ii) removing the bone harvester and the second bone core contained therein.

9. The method of claim 8, wherein the bone harvester is driven by impaction.

10. The method of claim 8, wherein the step of removing the bone harvester and the second bone core comprises retrograding the bone harvester from the bone.

11. The method of claim 7, wherein the bone harvester is driven by impaction.

12. The method of claim 7, wherein the step of removing the bone harvester and the first bone core comprises retrograding the bone harvester from the bone.

* * * * *

UNITED STATES PATENT AND TRADEMARK OFFICE
CERTIFICATE OF CORRECTION

PATENT NO. : 5,785,714  
DATED : Jul. 28, 1998  
INVENTOR(S) : Morgan et al.

It is certified that error appears in the above-indentified patent and that said Letters Patent is hereby corrected as shown below:

The title of the invention, as shown on the title page and in col. 1, is corrected to read as follows:

METHOD OF DOUBLE SOCKET ARTHROSCOPIC KNEE REPAIR

On the title page, after the date Filed, insert the following:

Related U.S. Application Data

[60]  Continuation of Ser. No. 08/389,492, filed February 16, 1995, Pat. No. 5,603,716.

UNITED STATES PATENT AND TRADEMARK OFFICE
CERTIFICATE OF CORRECTION

PATENT NO. : 5,785,714
DATED : Jul. 28, 1998
INVENTOR(S) : Morgan et al.

It is certified that error appears in the above-identified patent and that said Letters Patent is hereby corrected as shown below:

In col. 1, under the title of the invention, insert the following:

--This is a continuation of application Serial No. 08/389,492, filed February 16, 1995, now U.S. Pat. No. 5,603,716.--

Signed and Sealed this

Sixth Day of October, 1998

Attest:

BRUCE LEHMAN

*Attesting Officer*  *Commissioner of Patents and Trademarks*